United States Patent [19]

Hilderbrand

[11] Patent Number: 5,087,771
[45] Date of Patent: Feb. 11, 1992

[54] PROCESS FOR THE PURIFICATION OF MONOTERTIARYBUTYL HYDROQUINONE

[75] Inventor: James R. Hilderbrand, Kingsport, Tenn.

[73] Assignee: Eastman Kodak Company, Rochester, N.Y.

[21] Appl. No.: 622,453

[22] Filed: Dec. 5, 1990

[51] Int. Cl.⁵ ............................................. C07C 37/84
[52] U.S. Cl. .................................. 568/753; 568/749; 568/766
[58] Field of Search ............... 568/753, 780, 749, 766

[56] References Cited

U.S. PATENT DOCUMENTS

| 2,722,556 | 3/1952 | Young et al. | 568/766 |
| 4,493,719 | 1/1985 | Wintermantel et al. | |
| 4,507,244 | 3/1985 | von Rappard et al. | 62/532 |
| 4,720,570 | 1/1988 | Boyle | 568/70 |
| 4,861,919 | 8/1989 | Robbins et al. | 568/724 |

FOREIGN PATENT DOCUMENTS

| 60220197 | 4/1987 | Japan | 568/753 |
| 60221607 | 4/1987 | Japan | 568/753 |

Primary Examiner—Werren B. Lone
Attorney, Agent, or Firm—Mark A. Montgomery; William P. Heath, Jr.

[57] ABSTRACT

A process for producing food-grade tertiary-butyl hydroquinone from impure montertiary butyl hydroquinone is provided. Impure monotertiary butyl hydroquinone crystals are agitated at an elevated temperature while in contact with a non-polar solvent under conditions to extract the majority of the impurities followed by separating purified monotertiary butyl hydroquinone crystals from the solvent at a temperature above the crystallization point of the impurities.

15 Claims, No Drawings

PROCESS FOR THE PURIFICATION OF MONOTERTIARYBUTYL HYDROQUINONE

FIELD OF THE INVENTION

The present invention relates to the purification of monotertiarybutyl hydroquinone. More particularly the present invention relates to a process for producing food-grade tertiarybutyl hydroquinone from impure monotertiarybutyl hydroquinone.

BACKGROUND OF THE INVENTION

Monotertiarybutyl hydroquinone is well known and is prepared by different processes. U.S. Pat. No. 2,722,556 the disclosure of which is incorporated here by reference in its entirety, discloses a process for preparing monotertiarybutyl hydroquinone by reacting hydroquinone with isobutylene or tertiarybutyl alcohol. Pure or food-grade tertiarybutyl hydroquinone is obtained by purifying impure monotertiarybutyl hydroquinone. Food-grade tertiarybutyl hydroquinone is very desirable and is useful for preventing oxidation in food products, thus preserving freshness of flavor and aroma. The required specifications for food-grade tertiarybutyl hydroquinone are: Assay 99% Min., Arsenic 3 ppm Max., t-Butyl-p-benzoquinone 0.2% Max., Heavy Metals 10 ppm Max., Hydroquinone 0.1% Max., Toluene 0.0025% Max., and passing the Ultraviolet Absorbance Test.

The main impurity in monotertiarybutyl hydroquinone (MTBHQ) is the by-product of the alkylation of hydroquinone with isobutene, namely 2,5 ditertiarybutyl hydroquinone (DTBHQ). The current practice for the preparation of food-grade tertiarybutyl hydroquinone (TBHQ) is by recrystallization. This recrystallization entails completely dissolving crude water wet MTBHQ crystals in toluene, decanting the water and filtering the hot solution to a crystallizer. The MTBHQ is crystallized, and the majority of the DTBHQ remains in the toluene mother liquor. The toluene is removed from the wet crystals by further processing steps. The product is then isolated, dried and then pulverized prior to packaging for sale. This process is expensive and is very intensive in both labor and equipment requiring long batch cycle times and specialized equipment. Consequently, the cost to purify MTBHQ to food-grade TBHQ by this process is high.

Another possible purification of MTBHQ to food-grade TBHQ is distillation at high vacuum, however, the relative volatility of MTBHQ and DTBHQ is close to one so that the separation would require many stages of rectification and high reflux ratios. Operating under high vacuum at high temperature allows oxygen to enter the distillation column, causing some oxidation of the product. In addition, unless all traces of acid are neutralized, the temperatures required for distillation causes MTBHQ to dealkylate, producing hydroquinone which contaminates the product.

In light of the above, it would be very desirable to be able to produce food-grade TBHQ in a less complicated, less expensive process avoiding the above problems.

SUMMARY OF THE INVENTION

The process for producing food-grade tertiarybutyl hydroquinone comprises:

(a) agitating a mixture of impure monotertiarybutyl hydroquinone crystals containing 2,5 ditertiarybutyl hydroquinone, assaying between about 90 and 99 weight percent monotertiarybutyl hydroquinone on a dry basis, and a non-polar solvent at a temperature of about 80° C. to about 118° C. under conditions of pressure such that a sufficient amount of the solvent remains in the contacting vessel at the contacting temperature for a sufficient time to remove a majority of the impurities from the monotertiarybutyl hydroquinone; and (b) separating monotertiarybutyl hydroquinone crystals from the solvent at a temperature above the crystallization point of 2,5 ditertiarybutyl hydroquinone in the solvent, said crystals assaying 99.0 weight percent minimum monotertiarybutyl hydroquinone on a dry basis.

DETAILED DESCRIPTION OF THE INVENTION

The present invention is a new process for purifying MTHBQ to food-grade THBQ. This process entails only one product isolation whereas the prior art requires two isolations and multiple product vessels including a glass-lined vessel. The process according to the present invention for producing food-grade tertiarybutyl hydroquinone more preferably comprises:

(a) agitating a mixture of impure monotertiarybutyl hydroquinone and a non-polar, non-aromatic solvent at a temperature of about 80° C. to 118° C. under conditions to remove the majority of the impurities from the monotertiarybutyl hydroquinone; and (b) separating monotertiarybutyl hydroquinone crystals from the solvent at a temperature above the crystallization point of the impurities in the solvent.

The crude monotertiarybutyl hydroquinone is preferably prepared by the process disclosed in U.S. Pat. No. 2,722,556 the disclosure of which is incorporated herein by reference in its entirety. This process entails reacting hydroquinone with either isobutylene or tertiarybutyl alcohol in the presence of a strong acid catalyst. The thus produced MTHBQ is in the form of water wet crystals. The crude MTHBQ is relatively pure, assaying between about 95 and 99 weight percent MTHBQ on a dry basis.

The non-polar solvent should also be non-aromatic due to toxicity and environmental concerns. This non-polar, non-aromatic solvent is preferably a relatively high boiling solvent such that the mixture in (a) has a boiling point in the range of about 85° to about 115° C. at atmospheric pressure. This relatively high boiling solvent is preferably selected from n-heptane, octane, isooctane, cyclohexane, and naphtha. The more preferred non-polar, non-aromatic solvent is VM&P Naphtha having a flash point of about 10° C. (50° F.).

The amount of the solvent used in the purification or contacting step of the present invention, must be sufficient to dissolve essentially all of the DTBHQ impurity present in the crude MTBHQ without dissolving a significant amount of the MTBHQ crystals. This amount of solvent is preferably between about 70 and 95 weight percent based on the total weight of solvent and dry MTBHQ. The amount of solvent used in the process of the present invention is more preferably between about 80 and 90 weight percent with about 85 weight percent being most preferred.

The contacting or purification step of the present invention also preferably contains a water soluble reducing agent such as ascorbic acid, erythorbic acid, sodium hydrosulfite, sodium erythorbate, or sulfur dioxide. The preferred water soluble reducing agents are ascorbic acid and sodium hydrosulfite since these would not necessitate expensive corrosion resistant equipment.

The amount of water soluble reducing agent used in the process of the present invention is generally between about 0.1 and about 0.5 weight percent based on the total. The amount of reducing agent used in the process of the present invention is more preferably between about 0.15 and 0.4 with 0.2 weight percent being most preferred.

The first step of the process of the present invention more preferably entails agitating the mixture of impure MTBHQ and non-polar, non-aromatic solvent under reflux conditions to soften the MTBHQ crystals forming a slurry. This slurry is preferably agitated at or below reflux conditions for at least about 15 minutes up to 2 hours while returning the condensed vapors to the purification vessel. This temperature is preferably between about 85° and 105° C. with between about 90° and 95° C. being more preferred. The contacting time is more preferably between about 15 minutes and 60 minutes with about 30 minutes being most preferred.

If a non-polar non-aromatic solvent is chosen that boils lower than the desired purification temperature, then the pressure in the purification vessel must be increased to compensate.

The MTHBQ crystals in the purification vessel are preferably water wet containing about 20 to 40 weight percent water based on the total of water and dry MTBHQ. The mixture in the reaction vessel preferably contains between about 2 and 10 weight percent water based on the total. If water is removed by decantation during the contacting or purification step, the pot temperature has a tendency to rise to the normal boiling point of the solvent. At high temperatures, the MTBHQ tends to become light beige and degrades. Therefore, it is preferred that the amount of water in the purification vessel remain between about 3 and 9 weight percent with about 5 weight percent being most preferred.

The separation step in which the MTBHQ crystals are separated from the solvent must be conducted at a temperature above the crystallization point of the impurities in the solvent (DTBHQ etc.). Otherwise, the dissolved impurities will precipitate and contaminate the product. This temperature is preferably at least 50° C. or above and is more preferably not less than 60° C. The process of the present invention more preferably comprises a cooling step between the purification step (a) and the separation step (b). The mixture of (a) is preferably cooled to a temperature between about 60° and 80° C. with about 60° C. being more preferred. This cooling step is conducted for safety and environmental purposes and is not essential.

The process according to the present invention also preferably comprises a washing step after the separation step in which the MTBHQ crystals are washed with a polar solvent. The polar solvent is preferably water.

The process of the present invention also preferably entails a drying step at the end of the process. This drying step is preferably conducted under vacuum at a temperature between about 50° C. and 90° C. with about 65° C. and a vacuum of 25" Hg being most preferred.

The process according to the present invention more preferably comprises:

(a) agitating a mixture of (1) impure water wet crystals of monotertiarybutyl hydroquinone containing 2,5 ditertiarybutyl hydroquinone, assaying between about 95 and 99 weight percent monotertiarybutyl hydroquinone on a dry basis, (2) nonpolar, non-aromatic solvent, and (3) water soluble reducing agent at a temperature of about 80° to about 118° C. at about atmospheric pressure for at least about 15 minutes wherein the mixture has a boiling point in the range of about 85° to 115° C.;

(b) cooling the mixture of (a) to no lower than 50° C.;

(c) separating purified crystals of monotertiarybutyl hydroquinone from the solvent, and (d) washing the purified crystals with a polar solvent.

The following examples are set forth to illustrate the present invention and are not intended to limit the reasonable scope thereof.

EXAMPLES

EXAMPLE 1

This example illustrates the purification of crude, water-wet MTBHQ by the process of the present invention in VM&P Naphtha at 95° C. with some water removal. Into a 100-gallon stainless steel reactor, 450 pounds of VM&P Naphtha and 2.5 pounds of ascorbic acid were charged along with 110 pounds of crude, water-wet (74.3% solids) MTBHQ which assayed 98.1% MTBHQ, and 1.3% DTBHQ. The reactor was purged to remove air and the batch was heated to the reflux temperature of 92° C. under atmospheric pressure. The vapor was condensed, and the organic phase returned to the reactor. Condensed water was decanted from the organic phase and removed until the reactor temperature reached 95° C. The amount of water removed measured 14 pounds. The batch was heated under reflux for one hour at 95° C. The batch was cooled to 60° C. over a 1-hour time period and then filtered. Two 50-gallon washes of water were applied to the cake. The total cycle time was 6 hours. The wet cake was dried in a rotary vacuum dryer. The product weighed 74 pounds for a recovery of 94%. The assay of the product was 99.74% by gas chromatography, and all food-grade TBHQ product specifications were met.

EXAMPLE 2

This example illustrates the purification of crude, water-wet (77.1% solids) MTBHQ assaying 98.66% MTBHQ and 0.9% DTBHQ by the process of the present invention in VM&P naphtha at 92° C. with no water removal. To a 2-liter flask, 750 grams of naphtha, 3.5 grams of ascorbic acid, and 162.1 grams of crude, water-wet MTBHQ were charged. The flask was inerted and the contents heated to 85° C. over a 20-minute period. The batch was held at 85° C. for 45 minutes. The batch then was cooled to 60° C. over a 1-hour period. The hot naphtha was then sucked out of the flask using a glass fitted filter attached to a vacuum flask. Then 100 grams of virgin naphtha was added and mixed with the product. The solvent was again pulled away from the solids by vacuum through the glass fitted filter. Then 350 grams of cool water was added to the flask with agitation. The slurry was filtered at 20° C. and the cake washed with 350 grams of water and then dried in a vacuum oven overnight at 45° C. The assay of the product was 99.71% by gas chromatography, and all food-grade TBHQ specifications were met. The recovery was 92%.

EXAMPLE 3

This example is according to a less preferred process and illustrates the detrimental effect of low process temperature. To a 1-liter flask, 750 grams of VM&P Naphtha, 156.8 grams of crude, water-wet (79.7% solids) MTBHQ (assay 98.75% MTBHQ, and 0.77% DTBHQ), and one gram of sodium hydrosulfite were charged. The flask was inerted and heated to 75° C. over a 20-minute period at atmospheric pressure. The slurry was held for 2 hours at 75° C., cooled to 60° C., and filtered. The solids were washed with 260 grams of water followed by a 330-gram naphtha wash. The solids were dried in a vacuum oven at 45° C. The assay of the product was 99.51% MTBHQ by gas chromatography, but the DTBHQ content was 0.2% which equals the maximum limit for food-grade TBHQ. The recovery was 98%.

The invention has been described in detail with particular reference to preferred embodiment thereof, but it will be understood that variations and modifications can be affected within the spirit and scope of the present invention.

We claim:

1. A process for purifying monotertiarybutyl hydroquinone comprising:
    (a) agitating a mixture of impure monotertiarybutyl hydroquinone crystals containing 2,5 ditertiarybutyl hydroquinone, assaying between about 90 and 99 weight percent monotertiarybutyl hydroquinone on a dry basis, and a non-polar solvent at a temperature of about 80° C. to about 118° C. under conditions of pressure such that a sufficient amount of solvent remains in the contacting vessel at the contacting temperature for a sufficient time to remove a majority of impurities from the monotertiarybutyl hydroquinone; and
    (b) separating monotertiarybutyl hydroquinone crystals from the solvent at a temperature above the crystallization point of 2,5 ditertiarybutyl hydroquinone in the solvent, said crystals assaying 99.0 weight percent minimum monotertiarybutyl hydroquinone on a dry basis.

2. The process according to claim 1 wherein the non-polar solvent is also a non-aromatic solvent 3. The process according to claim 2 wherein said solvent is selected from n-heptane, octane, isooctane, cyclohexane, and naphtha.

4. The process according to claim 2 wherein step (a) is conducted at about atmospheric pressure and the non-polar, non-aromatic solvent is a relatively high boiling solvent such that the mixture in (a) has a boiling point between about 85° and about 115° C.

5. The process according to claim 1 wherein said monotertiarybutyl hydroquinone is in the form of water-wet crystals that have been prepared by reacting hydroquinone with either isobutylene, or tertbutyl alcohol in the presence of a strong acid catalyst assaying between about 95 and 99 weight percent monotertiarybutyl hydroquinone.

6. The process according to claim 1 wherein the amount of non-polar solvent used in Step (a) is between about 70 and about 95 weight percent based on the total weight of solvent and dry monotertiarybutyl hydroquinone.

7. The process according to claim 1 wherein the mixture in (a) contains about 2 to about 10 weight percent water based on the total.

8. The process according to claim 1 wherein the mixture in Step (a) also contains about 0.1 to about 0.5 wt. % of a water soluble reducing agent selected from the group consisting of ascorbic acid, erythorbic acid, sodium hydrosulfite, sodium erythorbate, and sulfur dioxide.

9. The process according to claim 1 wherein Step (a) is conducted at or below reflux conditions at a temperature between about 85° and about 105° C. for a time between about 15 minutes and about 2 hours.

10. The process according to claim 1 wherein Step (b) is conducted at a temperature of at least 50° C.

11. The process according to claim 1 further comprising a cooling step between Step (a) and Step (b) wherein the mixture of Step (a) is cooled to a temperature between about 60° and about 80° C.

12. The process according to claim 1 further comprising:
    (c) washing the separated purified monotertiarybutyl hydroquinone crystals with a polar solvent; and
    (d) drying the washed monotertiarybutyl hydroquinone crystals.

13. The process according to claim 12 wherein said polar solvent is water.

14. A process for purifying monotertiarybutyl hydroquinone comprising:
    (a) agitating a mixture of (1) impure water wet crystals of monotertiarybutyl hydroquinone containing 2,5 ditertiarybutyl hydroquinone, assaying between about 95 and 99 weight percent monotertiarybutyl hydroquinone on a dry basis, (2) non-polar, non-aromatic solvent, and (3) water soluble reducing agent selected from the group consisting of ascorbic acid, erythorbic acid, sodium hydrosulfite, sodium erythorbate, and sulfur dioxide at a temperature of about 80° to about 118° C. at about atmospheric pressure for at least about 15 minutes wherein the mixture has a boiling point in the range of about 85° to about 115° C.;
    (b) cooling the mixture of (a) to no lower than 50° C.;
    (c) separating purified crystals of monotertiarybutyl hydroquinone from the solvent; and
    (d) washing the purified crystals with a polar solvent.

15. A process for purifying monotertiarybutyl hydroquinone comprising:
    (a) agitating a mixture of (1) impure water wet crystals of monotertiarybutyl hydroquinone containing 2,5 ditertiarybutyl hydroquinone, assaying between about 95 and 99 weight percent monotertiarybutyl hydroquinone on a dry basis, (2) naphtha present in a concentration between about 75 and about 85 weight percent based on the total, and (3) water soluble reducing agent selected from ascorbic acid and sodium hydrosulfite at a temperature between about 85° and about 105° C. at about atmospheric pressure for a time between about 15 minutes and 2 hours wherein the mixture has a boiling point in the range of about 85° to 115° C.;
    (b) cooling the mixture of (a) to no lower than 50° C.;
    (c) separating purified crystals of monotertiarbutyl hydroquinone from the solvent; and
    (d) washing the purified crystals with a polar solvent.

* * * * *